(12) United States Patent  
Cannesson

(10) Patent No.: US 8,532,754 B2  
(45) Date of Patent: Sep. 10, 2013

(54) METHOD AND APPARATUS FOR ASSESSMENT OF FLUID RESPONSIVENESS

(75) Inventor: Maxime Cannesson, Irvine, CA (US)

(73) Assignee: Sironis, Inc., Newport Beach, CA (US)

( * ) Notice: Subject to any disclaimer, the term of this patent is extended or adjusted under 35 U.S.C. 154(b) by 137 days.

(21) Appl. No.: 13/095,827

(22) Filed: Apr. 27, 2011

(65) Prior Publication Data

US 2011/0270111 A1     Nov. 3, 2011

Related U.S. Application Data

(60) Provisional application No. 61/328,641, filed on Apr. 28, 2010.

(51) Int. Cl.
*A61B 5/0452*     (2006.01)

(52) U.S. Cl.
USPC .......................................... 600/509; 600/517

(58) Field of Classification Search
USPC ................... 600/508, 509, 517, 521
See application file for complete search history.

(56) References Cited

U.S. PATENT DOCUMENTS

| | | | |
|---|---|---|---|
| 6,776,764 | B2 | 8/2004 | Pinsky |
| 7,225,013 | B2 | 5/2007 | Geva et al. |
| 7,422,562 | B2 | 9/2008 | Hatib |
| 8,298,151 | B2 | 10/2012 | Riobo |
| 2009/0192397 | A1 * | 7/2009 | Fischell et al. ................ 600/516 |

OTHER PUBLICATIONS

Cannesson et al, Relations between respiratory changes in R-wave amplitude and arterial pulse pressure in mechanically ventilated patients, Journal of Clinical Monitoring, 2010, 24-203-207.

Giraud et al. Respiratory change in ECG-wave amplitude is a reliable parameter to estimate intravascular volume status, 2012, , J. Clin. Monit. Comput. (Published online on Nov. 2, 2012).

* cited by examiner

*Primary Examiner* — Joseph Stoklosa

(74) *Attorney, Agent, or Firm* — Mateo Aboy; Aboy & Associates PC

(57) ABSTRACT

Disclosed embodiments include a method for assessing fluid responsiveness implemented in a medical apparatus, a medical system, or a digital computer with one or more processors comprising: (a) measuring an electrocardiogram signal, and (b) computing a dynamic index predictive of fluid responsiveness from said electrocardiogram by calculating the R-wave amplitude variability over one or more respiratory cycles. According to one particular embodiment, the ECG changes in R-wave amplitude are calculated from the DII lead to generate a dynamic index to guide fluid therapy.

16 Claims, 4 Drawing Sheets

METHOD AND APPARATUS FOR ASSESSMENT OF FLUID RESPONSIVENESS

CROSS-REFERENCE TO RELATED APPLICATIONS

This application claims the benefit of U.S. Provisional Application No. 61/328,641 filed on Apr. 28, 2010 by the present inventor, which is incorporated herein by reference.

TECHNICAL FIELD

Disclosed embodiments relate to methods and apparatuses for cardiac monitoring. Specifically, they relate to methods and apparatus for dynamic estimation of fluid responsiveness.

BACKGROUND

Indicators and methods for noninvasive determination of fluid status of patients are important for monitoring of the condition of critical care patients. In many critical care settings clinicians must decide whether patients should be given intravenous fluid boluses and other therapies to improve perfusion. Excessive fluid can be damaging by impairing lung function when it decreases oxygen delivery to tissues and contributes to organ failure. Insufficient fluid can result in insufficient tissue perfusion which can also contribute to organ failure. Determining the best course of fluid therapy for a given patient is difficult and clinicians have few clinical signs to guide them.

Fluid administration in hemodynamically unstable patients is often a major challenge when it comes to measuring hemodynamic parameters in real time. Correct clinical assessment of hypovolemia is difficult, as is the decision to undertake fluid resuscitation as the initial treatment strategy. Specifically, it is very difficult to predict whether a hemodynamically unstable patient will respond to fluid therapy with an increase in stroke volume (SV) and cardiac output (CO). Moreover, fluid overload can cause significant pulmonary or cardiac dysfunction, whereas fluid insufficiency may cause tissue damage resulting in vital organ dysfunction. A patient's fluid responsiveness is the major and most important determinant to assess the adequacy of fluid resuscitation therapy and to ensure optimal cardiac performance and organ perfusion.

There are several dynamic parameters that can be used to assess fluid responsiveness from arterial blood pressure (ABP) and in some cases from plethysmogram signals. Several bedside indicators of ventricular preload have been used as predictors of fluid responsiveness. Right arterial pressure (RAP) and pulmonary artery occlusion pressure (PAOP) are commonly used in the intensive care unit (ICU) when deciding to administer fluids. Other bedside indicators of ventricular preload include right ventricular end diastolic volume (RVEDV) and left ventricular end diastolic area (LVEDA) measured with transesophageal echocardiography. Several studies and case reports have shown, however, that these static indicators based on cardiac filling pressures many have poor predictive value and often fail to give adequate information about fluid responsiveness.

Published studies have confirmed the clinical significance of monitoring the variations observed in left ventricular stroke volume that result from the interaction of the cardiovascular system and the lungs under mechanical ventilation. These stroke volume variations (SVV) are caused by the cyclic increases and decreases in the intrathoracic pressure due to the mechanical ventilation, which lead to variations in the cardiac preload and afterload. SVV has recently been extensively investigated and several studies have shown the usefulness of using SVV as predictor of fluid responsiveness in various clinical situations. Several other parameters based on SVV have been found to be useful as well. In particular, systolic pressure variation (SPV) with its delta-Up and delta-Down components has been found to be a very useful predictor of fluid responsiveness. SPV is based on the changes in the arterial pulse pressure due to respiration-induced variations in stroke volume. Yet another parameter that has recently been investigated and shown to be a valid indicator of fluid responsiveness is the pulse pressure variation (PPV).

Dynamic indicators based on cardiopulmonary interactions are accurate predictors of fluid responsiveness in mechanically ventilated patients under general anesthesia. Published studies have demonstrated that respiratory variations in arterial pulse pressure (PPV) were able to predict fluid responsiveness with good sensitivity and specificity in this setting.

The PPV index is a measure of the respiratory effect on the variation of systemic arterial blood pressure in patients receiving full mechanical ventilation. It is a dynamic predictor of increases in cardiac output due to an infusion of fluid. Published studies have demonstrated that PPV is one of the most sensitive and specific predictors of fluid responsiveness. Specifically, PPV has been shown to be useful as a dynamic indicator to guide fluid therapy in different patient populations receiving mechanical ventilation. For instance, PPV was found to exhibit better performance as a predictor of fluid responsiveness in patients before off-pump coronary artery bypass grafting than standard static pre-load indexes. PPV has also been shown to be useful for predicting and assessing the hemodynamic effects of volume expansion and a reliable predictor of fluid responsiveness in mechanically ventilated patients with acute circulatory failure related to sepsis. Another study concluded that PPV can be used to predict whether or not volume expansion will increase cardiac output in postoperative patients who have undergone coronary artery bypass grafting. A critical review of studies investigating predictive factors of fluid responsiveness in intensive care unit patients concluded that PPV and other dynamic parameters should be used preferentially to static parameters to predict fluid responsiveness.

The standard method for calculating PPV often requires simultaneous recording of arterial and airway pressure. Pulse pressure (PP) is calculated on a beat-to-beat basis as the difference between systolic and diastolic arterial pressure. Maximal PP ($PP_{max}$) and minimal PP ($PP_{min}$) are calculated over a single respiratory cycle, which is determined from the airway pressure signal. Pulse pressure variations PPV are calculated in terms of $PP_{max}$ and $PP_{min}$ and expressed as a percentage, $$PPV(\%) = 100 \times \frac{PP_{max} - PP_{min}}{(PP_{max} + PP_{min})/2} \quad (1)$$

SUMMARY

Currently there are no indices designed to predict fluid responsiveness or guide fluid therapy based on the electrocardiogram signal (ECG). ECG monitoring is of common use in anesthesiology and in intensive care medicine. Compared to arterial blood pressure, ECG has the advantage of being noninvasive.

Disclosed embodiments include a method for assessing fluid responsiveness implemented in a medical apparatus, a medical system, and/or a digital computer with one or more processors comprising: (a) measuring an electrocardiogram signal, and (b) computing a dynamic index predictive of fluid responsiveness from said electrocardiogram by calculating the R-wave amplitude variability over one or more respiratory cycles. According to one particular embodiment, and without limitation, ECG changes in R-wave amplitude (i.e., R-wave amplitude variability) are calculated from the DII lead to generate a dynamic index to guide fluid therapy ($\Delta$RDII).

DETAILED DESCRIPTION

Disclosed embodiments are illustrated by way of example, and not by way of limitation, in the figures of the accompanying drawings.

DETAILED DESCRIPTION

Electrocardiogram (ECG) monitoring is of common use in anesthesiology and in intensive care medicine. Disclosed embodiments are based on quantification of changes in ECG morphology that reflect changes in volume status. Respiratory variations in R-wave amplitude are related to respiratory variations in arterial pulse pressure (i.e. the pulse pressure variation index). Resistivity of the intracardiac blood being less than resistivity of tissues surrounding the heart, there is an enhancement of the radial and diminution of tangential electrical forces transmitted to the body surface. Accordingly, a decrease in intracardiac volume leads to a decrease in the QRS potentials, while increases in the volume results in increases in QRS amplitude. In respiratory R-wave variations intracardiac volume is cyclically modified resulting in stroke volume variations and the body electrical properties are not modified over a respiratory cycle.

A. Method and Apparatus Description

Disclosed embodiments include a method for assessing fluid responsiveness comprising: (a) measuring an electrocardiogram signal, and (b) calculating a dynamic indicator of fluid responsiveness obtained from said electrocardiogram signal by calculating the R-wave amplitude variability over one or more respiratory cycles. According to a particular embodiment the electrocardiogram signal is obtained from a mechanically ventilated patient under general anesthesia.

According to one particular embodiment, and without limitation, ECG changes in R-wave amplitude (i.e. R-wave amplitude variability) are calculated from the DII lead in order to generate a dynamic index to guide fluid therapy ($\Delta$RDII). In other alternative possible embodiments the dynamic indicator of fluid responsiveness is calculated from R-wave amplitude changes in a plurality of electrocardiogram leads. Furthermore, these R-wave amplitude changes can be combined in order to arrive at a final dynamic index.

Figure 1:
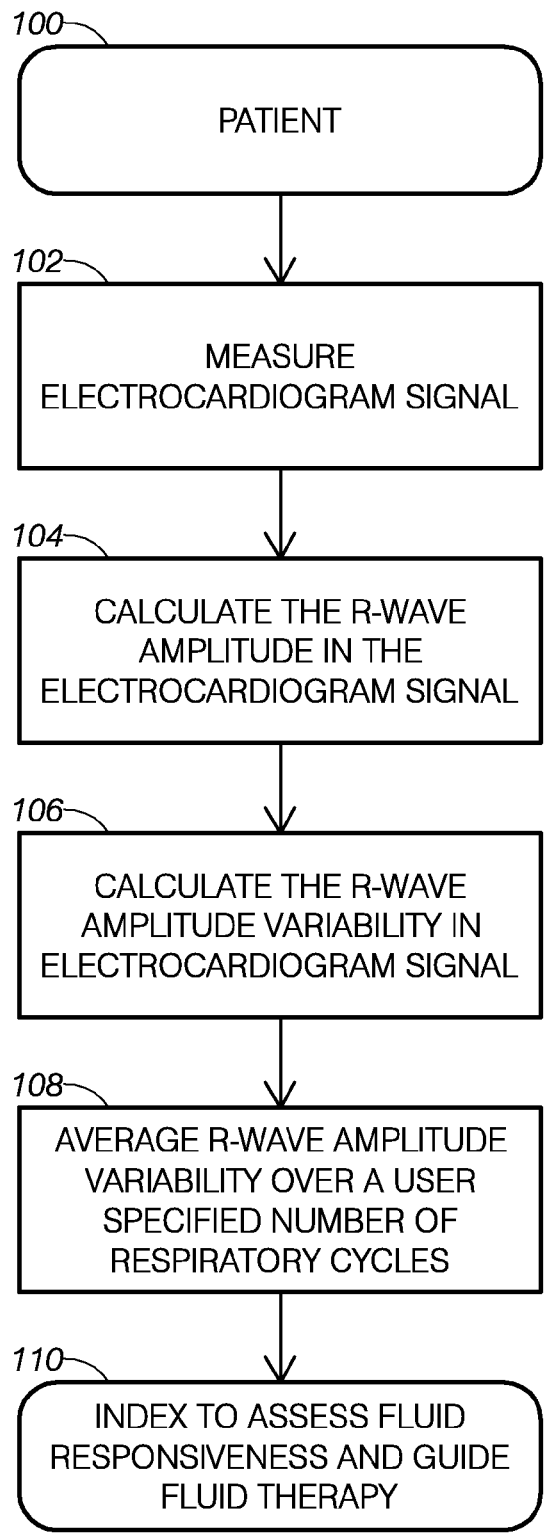
FIG. 1 shows a block diagram of the method according to one embodiment.

FIG. 1 shows the block diagram corresponding to an embodiment of the method for guiding fluid therapy implemented in a medical apparatus. According to this embodiment, a medical system or computer (i.e. a hardware device comprising one or more processors, data acquisition, data storage, and or more input/output devices including a display and a printer) acquires an electrocardiogram signal 102 from a patient 100 using ECG acquisition hardware. After measuring the electrocardiogram signal in the ECG acquisition module 102, a second system module calculates the R-wave amplitude 104, based on this amplitude a third module calculates the R-wave amplitude variability 106 and this output is averaged 108 over a user-specified number of respiratory cycles (for instance 2 to 10 respiratory cycles) to generate a smooth version of the dynamic index to guide fluid therapy that is reported by the system 110 in one or more output devices (e.g., display, printer). In particular embodiments, the ECG signal is acquired from patients 100 that are mechanically ventilated under general anesthesia. Furthermore, since ECG changes in R-wave amplitude from the DII lead are induced by marked and rapid LV preload alterations, a particular embodiment and without limitation, ECG changes in R-wave amplitude (i.e. R-wave amplitude variability) are calculated from the DII lead in order to generate a dynamic index to guide fluid therapy ($\Delta$RDII). According to a particular embodiment, said dynamic indicator of fluid responsiveness is further compared against one or more threshold values in order to classify patients according to their fluid responsiveness. In other embodiments, the assessment of fluid responsiveness is based on the R-wave amplitude variability, as well as the variability of other PQRST parameters in the ECG waveform (i.e., the relative changes and variability on the P, Q, R, S, and T complexes of ECG).

While particular embodiments have been described, it is understood that, after learning the teachings contained in this disclosure, modifications and generalizations will be apparent to those skilled in the art without departing from the spirit of the disclosed embodiments.

B. Validation and Testing of the Method According to One Embodiment.

The following description presents the experimental results obtained in a study conducted to determine the correlation of between ECG changes in R-wave amplitude (i.e. R-wave amplitude variability) calculated from the DII lead in order to demonstrate that the invention works for its intended purpose. The study compares one embodiment of the proposed dynamic index to guide fluid therapy ($\Delta$RDII) and the established dynamic indicator of fluid responsiveness (i.e. PPV). These results indicate $\Delta$RDII is correlated with PPV and can be used to asses fluid status.

B.1. Patients

Ethics approval to conduct this study was given by the Institutional Review Board (Comité Consultatif de Protection des Personnes dans la Recherche Biomédicale Lyon B, Hospices Civils de Lyon, France). Twenty-four sedated patients receiving mechanical ventilation in the postoperative period of cardiac surgery were studied. All patients gave written informed consent. Patients with spontaneous breathing, cardiac arrhythmias, left ventricular dysfunction (LV ejection fraction<50%), right ventricular failure, intracardiac shunt and age <18 years were excluded. Inclusion criteria were as follows: (1) instrumentation with a 6 cm 5 Fr tipped arterial radial catheter (Arrow International Inc., Reading, Pa., USA), (2) hemodynamic stability (defined as a variation in heart rate and blood pressure of less than 10% over the 15-min period before starting the protocol), and (3) monitoring of electrocardiographic waveform using a 5 lead ECG device.

B.2. Hemodynamic Measurements

B.2.1. Respiratory Variations in Arterial Pulse Pressure

Respiratory variations in arterial pulse pressure (PPV) were calculated using a standard monitor (Intellivue MP70, Philips Medical Systems, Suresnes, France). Pulse pressure (PP) was defined as the difference between systolic and diastolic pressure. Maximal (PPmax) and minimal (PPmin) values were determined over the same respiratory cycle.

$$PPV(\%) = 100 \times \frac{PP_{max} - PP_{min}}{(PP_{max} + PP_{min})/2} \quad (2)$$

The measurements were repeated on three consecutive respiratory cycles and averaged for statistical analysis.

B.2.2. Respiratory Variation in Electrocardiogram Analysis

The electrocardiogram was recorded using a standard monitor (Intellivue MP70, Philips Medical Systems, Suresnes, France). The ECG waveforms were analyzed by an observer (GK) blinded to the arterial waveforms. The R wave amplitude was calculated. Maximal RDII (RDIImax) and minimal RDII (RDIImin) were determined over the same respiratory cycle. To assess ΔRDII, the percent change was calculated as:

$$\Delta RDII = 100 \times \frac{RDII_{max} - RDII_{min}}{(RDII_{max} + RD_{min})/2} \quad (3)$$

The measurements were repeated on three consecutive respiratory cycles and averaged for statistical analysis. It is important to emphasize that many other substantially equivalent methods for calculating ΔRDII are possible.

B.3. Respiratory Parameters

All patients in this study received mechanical ventilation in a volume controlled mode with a tidal volume of 8 ml/kg and an inspiratory:expiratory ratio of 1:1 to 1:2. Positive end expiratory pressure (PEEP) was between 0 and 5 cm H2O. Breathing rate was 15/min.

B.4. Statistical Analysis

Linear correlation between PPV (ΔPP) and ΔRDII was tested using the Spearman rank method. PPV (ΔPP) and ΔRDII were compared using the Bland-Altman analysis. Data are presented as mean±SD. Receiver operating characteristic (ROC) curve was generated for ΔRDII varying the discriminating threshold of this parameter to determine the ability of ΔRDII to discriminate between patients with a PPV >13% and patients with a PPV ≦13%. Interobserver variability (GK, OD) for ΔRDII measurement was assessed using the Bland-Altman analysis. In all cases, a p value less than 0.05 was considered statistically significant.

B.5. Study Results

Figure 2:
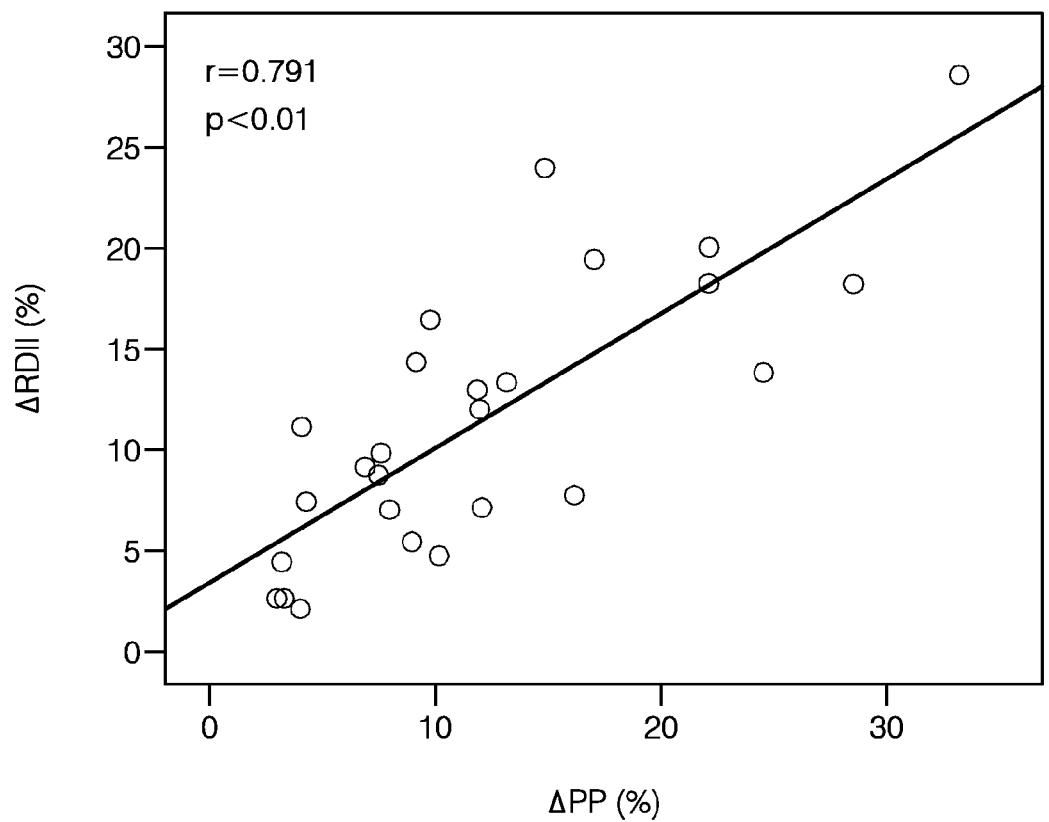
FIG. 2 shows a correlation plot between arterial blood pressure pulse pressure variation (PPV) and ECG amplitude variation calculated from the DII lead ($\Delta$RDII).
Figure 3:
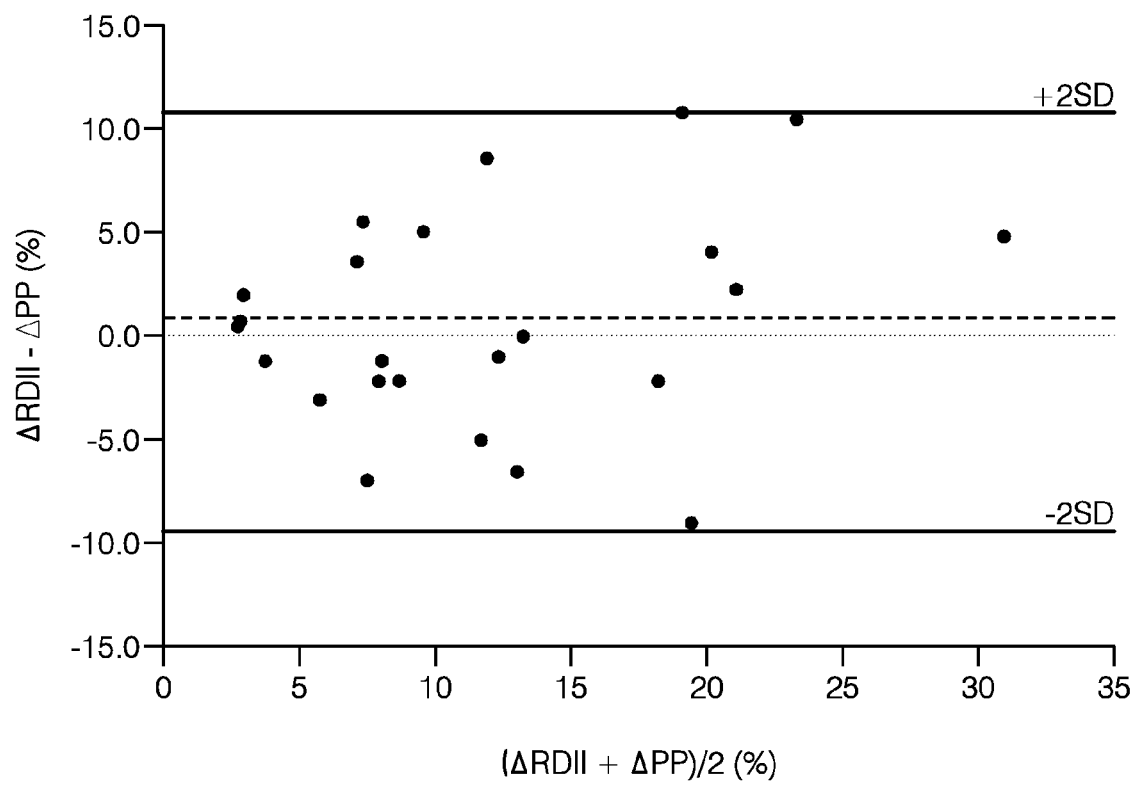
FIG. 3 shows a Bland-Altman analysis plot showing the agreement between ($\Delta$RDII) and PPV.
Figure 4:
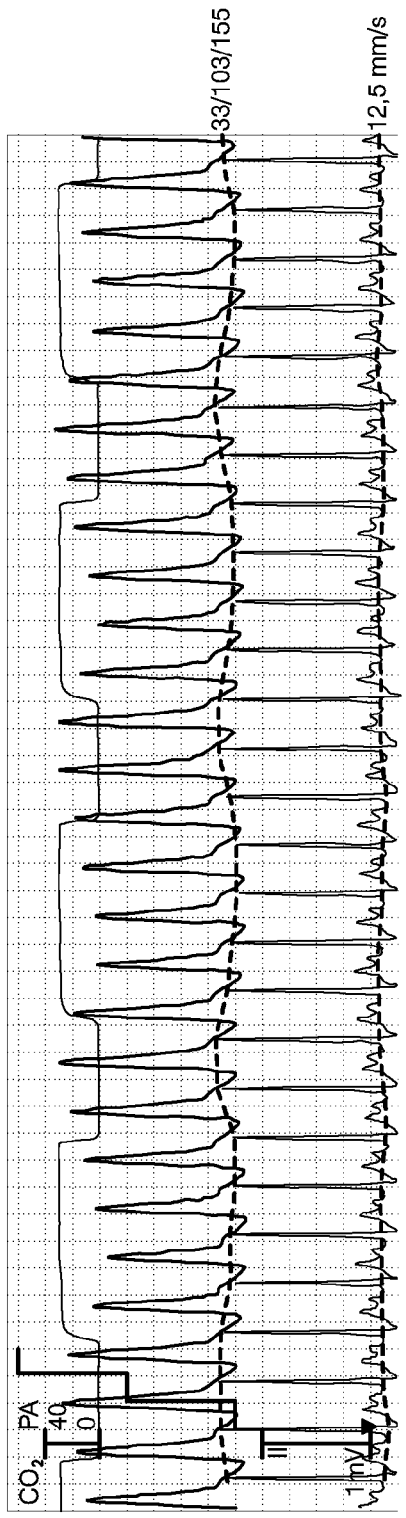
FIG. 4 shows a simultaneous recording of expiratory CO2, ECG in lead II and arterial pressure waveforms in two illustrative patients.
Figure 4:
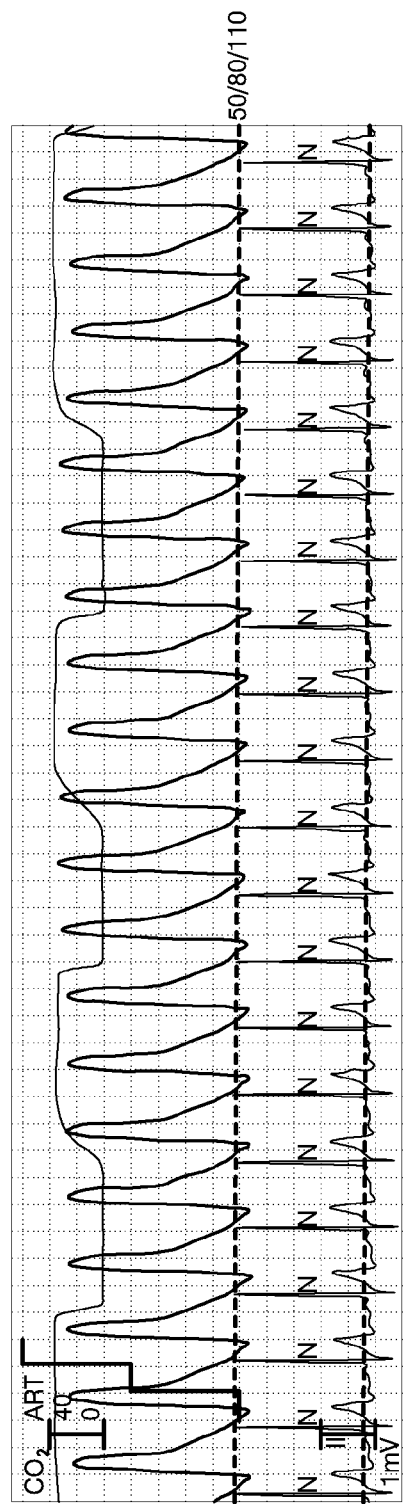

As shown in FIG. 2 the study results indicate there is a statistically significant relationship between PPV (ΔPP) and ΔRDII (r=0.79, p<0.01). The agreement between PPV (ΔPP) and ΔRDII was 0.69±5.24%. FIG. 3 shows an example of simultaneous recording of expiratory CO2, arterial pressure and ECG lead II in two illustrative patients. Top of the figure shows a patient exhibiting important respiratory variations in arterial pulse pressure and in R-wave amplitude. The other patient shows small respiratory variations in arterial pulse pressure and in R-wave amplitude. The threshold ΔRDII value of 13% allowed discrimination between patients with a PPV >13% and patients with a PPV ≦13% with a sensitivity of 89% and a specificity of 88%. Interobserver variability for ΔRDII measurement was 2.1±2.4%. FIG. 4 shows a simultaneous recording of expiratory CO2, ECG in lead II and arterial pressure waveforms in two illustrative patients.

While particular embodiments have been described, it is understood that, after learning the teachings contained in this disclosure, modifications and generalizations will be apparent to those skilled in the art without departing from the spirit of the disclosed embodiments. It is noted that the foregoing embodiments and examples have been provided merely for the purpose of explanation and are in no way to be construed as limiting. While the method and corresponding medical apparatus has been described with reference to various embodiments, it is understood that the words which have been used herein are words of description and illustration, rather than words of limitation. Further, although the embodiments have been described herein with reference to particular means, materials and embodiments, the actual embodiments are not intended to be limited to the particulars disclosed herein; rather, they extend to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosed embodiments in its aspects.

The invention claimed is:

1. A method for assessment of fluid responsiveness implemented in a medical apparatus, said method comprising:
   (a) obtaining an electrocardiogram signal;
   (b) calculating a R-wave amplitude from said electrocardiogram signal over one or more respiratory cycles;
   (c) computing a dynamic indicator of fluid responsiveness from said R-wave amplitude; and
   (d) outputting said dynamic indicator for assessment of fluid responsiveness.

2. The method of claim 1, wherein said dynamic indicator for assessment of fluid responsiveness is calculated from R-wave amplitude changes in one or more electrocardiogram leads.

3. The method of claim 2, wherein said R-wave amplitude changes in one or more electrocardiogram leads includes at least the R-wave amplitude changes of a DII positioned lead (ΔRDII).

4. The method of claim 3, wherein said dynamic indicator for assessment of fluid responsiveness is further compared against one or more fluid responsiveness threshold values configured to classify patients according to their fluid responsiveness.

5. A medical apparatus for assessment of fluid responsiveness, said apparatus comprising:
   (a) a signal acquisition circuit to acquire an electrocardiogram signal;
   (b) a memory to store said electrocardiogram signal;
   (c) a processor configured to perform the processing step of calculating a R-wave amplitude from said electrocardiogram signal over one or more respiratory cycles and computing a dynamic indicator of fluid responsiveness from said R-wave amplitude; and
   (d) an output device for outputting said dynamic indicator for assessment of fluid responsiveness.

6. The medical apparatus of claim 5, wherein said dynamic indicator for assessment of fluid responsiveness is calculated from R-wave amplitude changes in one or more electrocardiogram leads.

7. The medical apparatus of claim 6, wherein said R-wave amplitude changes in one or more electrocardiogram leads includes at least the R-wave amplitude changes of a DII lead (ΔRDII).

8. The medical apparatus of claim 7, wherein said dynamic indicator for assessment of fluid responsiveness is further compared against one or more threshold values in order to classify patients according to their fluid responsiveness.

9. The method of claim 1, wherein said computing a dynamic indicator of fluid responsiveness from said R-wave amplitude comprises calculating a respiratory variation in R-wave amplitude.

10. The method of claim 9, wherein said respiratory variation in R-wave amplitude comprises calculating the maximum amplitude in said R-wave and the minimum amplitude in said R-wave during a respiratory cycle.

11. The method of claim 10, wherein said respiratory variation in R-wave amplitude further comprises calculating a R-wave respiratory variation index (ΔR) correlated with changes in a R-wave amplitude from a DII positioned lead (ΔRDII), said changes in said R-wave amplitude from said DII positioned lead computed according to an equation defined by $$\Delta RDII = 100 \times \frac{RDII_{max} - RDII_{min}}{(RDII_{max} + RD_{min})/2},$$

where $RDII_{max}$ denotes the maximum amplitude in said DII lead R-wave during a respiratory cycle and $RDII_{min}$ denotes the minimum amplitude in said DII lead R-wave during said respiratory cycle.

12. The method of claim 11, wherein said respiratory variation in R-wave amplitude further comprises averaging measurements of said R-wave amplitude over three or more respiratory cycles.

13. The method of claim 12, wherein said computing a dynamic indicator of fluid responsiveness from said R-wave amplitude further comprises comparing said respiratory variation in R-wave amplitude against a fluid responsiveness threshold.

14. The method of claim 12, wherein said fluid responsiveness threshold is equal to or greater than 13% of said ΔRDII index.

15. The method of claim 13, wherein said computing a dynamic indicator of fluid responsiveness further comprises obtaining said respiratory variation in R-wave amplitude from an electrocardiogram signal of a patient under mechanical ventilation.

16. The method of claim 1, wherein said computing a dynamic indicator of fluid responsiveness from said R-wave amplitude further comprises (a) calculating a respiratory variation of one or more PQRST parameters of said electrocardiogram obtained during mechanical ventilation of patients under general anesthesia, (b) averaging said respiratory variation over three or more respiratory cycles, and (c) comparing said variation against a fluid responsiveness threshold.

* * * * *